(12) United States Patent
Lynn (10) Patent No.: US 11,952,269 B1
(45) Date of Patent: *Apr. 9, 2024

(54) SYSTEM FOR GENERATING AQUEOUS OZONE SOLUTION WITH VARIABLY CONTROLLED OZONE GENERATOR AND PIPE ASSEMBLY FOR IN-LINE MIXING

(71) Applicant: Daniel W. Lynn, Omaha, NE (US)

(72) Inventor: Daniel W. Lynn, Omaha, NE (US)

(*) Notice: Subject to any disclaimer, the term of this patent is extended or adjusted under 35 U.S.C. 154(b) by 0 days.

This patent is subject to a terminal disclaimer.

(21) Appl. No.: 18/328,873

(22) Filed: Jun. 5, 2023

Related U.S. Application Data (63) Continuation-in-part of application No. 17/862,506, filed on Jul. 12, 2022, which is a continuation of
(Continued)

(51) Int. Cl.
| | | |
|---|---|---|
| *C01B 13/11* | (2006.01) | |
| *A61L 2/18* | (2006.01) | |
| *B01F 23/232* | (2022.01) | |
| *B01F 25/312* | (2022.01) | |
| *C02F 1/78* | (2023.01) | |
| *C11D 3/48* | (2006.01) | |

(Continued)

(52) U.S. Cl.
CPC .............. *C01B 13/11* (2013.01); *A61L 2/183* (2013.01); *B01F 23/2323* (2022.01); *B01F 25/31242* (2022.01); *C02F 1/78* (2013.01); *C11D 3/48* (2013.01); *C11D 7/04* (2013.01); *A61L 2202/11* (2013.01); *B01F 23/237613* (2022.01); *C02F 2201/782* (2013.01); *C02F 2209/04* (2013.01); *C02F 2209/40* (2013.01); *C02F 2303/04* (2013.01); *C11D 2111/14* (2024.01); *C11D 2111/44* (2024.01)

(58) Field of Classification Search
USPC ...................................................... 204/157.5
See application file for complete search history.

(56) References Cited

U.S. PATENT DOCUMENTS

| | | | | |
|---|---|---|---|---|
| 3,150,070 A | * | 9/1964 | Masahiko | ............. C01B 13/115 422/186.14 |
| 6,153,105 A | | 11/2000 | Tadlock et al. | |

(Continued)

OTHER PUBLICATIONS

International Search Report and Written Opinion for PCT/US2021/047089 dated Nov. 12, 2021.

*Primary Examiner* — Hayden Brewster
(74) *Attorney, Agent, or Firm* — Nasr Patent Law LLC; Faisal K. Abou-Nasr (57) ABSTRACT

A system for generating aqueous ozone solution employs a variably controlled ozone generator and at least one pipe assembly for in-line mixing of ozone into water that is supplied to the system. The pipe assembly includes a first flow path for water to flow through. The first flow path includes one or more ozone intake ports that are fluidically coupled to the ozone generator. The pipe assembly further includes a second flow path fluidically coupled in parallel with the first flow path. The second flow path includes a control valve that selectively permits a portion of the water to flow through the second flow path to produce a negative pressure in the first flow path so that ozone is drawn into the first flow path through the one or more ozone intake ports and mixed into the water flowing through the first flow path.

18 Claims, 9 Drawing Sheets

Related U.S. Application Data application No. 17/722,613, filed on Apr. 18, 2022, now Pat. No. 11,383,979, which is a continuation-in-part of application No. 17/672,547, filed on Feb. 15, 2022, now Pat. No. 11,352,256, which is a continuation-in-part of application No. 17/408,742, filed on Aug. 23, 2021, now Pat. No. 11,247,899, which is a continuation-in-part of application No. 17/168,911, filed on Feb. 5, 2021, now Pat. No. 11,097,946, which is a continuation-in-part of application No. 17/150,449, filed on Jan. 15, 2021, now Pat. No. 11,078,079, which is a continuation-in-part of application No. 17/078,799, filed on Oct. 23, 2020, now Pat. No. 11,305,991, which is a continuation of application No. 15/476,326, filed on Mar. 31, 2017, now abandoned, which is a continuation-in-part of application No. 15/446,331, filed on Mar. 1, 2017, now Pat. No. 10,232,070, which is a continuation-in-part of application No. 15/355,884, filed on Nov. 18, 2016, now abandoned, which is a continuation-in-part of application No. 15/050,777, filed on Feb. 23, 2016, now abandoned.

(60) Provisional application No. 62/121,770, filed on Feb. 27, 2015.

(51) Int. Cl.
*C11D 7/04* (2006.01)
*B01F 23/237* (2022.01)

(56) References Cited

U.S. PATENT DOCUMENTS

| | | | |
|---|---|---|---|
| 6,334,328 | B1 | 1/2002 | Brill |
| 6,685,825 | B1 | 2/2004 | Chang |
| 8,071,526 | B2 | 12/2011 | Lynn |
| 8,075,705 | B2 | 12/2011 | Lynn |
| 9,068,149 | B2 | 6/2015 | Lynn |
| 9,151,528 | B2 | 10/2015 | Erbs et al. |
| 9,174,845 | B2 | 11/2015 | Lynn |
| 9,522,348 | B2 | 12/2016 | Lynn |
| 11,097,946 | B1 * | 8/2021 | Lynn .................... C11D 2111/44 |
| 11,247,899 | B2 * | 2/2022 | Lynn ........................ C11D 3/48 |
| 11,352,256 | B1 * | 6/2022 | Lynn ........................ C11D 3/48 |
| 11,383,979 | B1 * | 7/2022 | Lynn .................... B01F 23/2323 |
| 11,591,216 | B2 * | 2/2023 | Lynn ................. B01F 25/31242 |
| 11,827,547 | B1 * | 11/2023 | Lynn ....................... B01F 23/23 |
| 2002/0127158 | A1 | 9/2002 | Holsclaw et al. |
| 2004/0004042 | A1 | 1/2004 | Hadley et al. |
| 2004/0074252 | A1 | 4/2004 | Shelton |
| 2004/0168989 | A1 | 9/2004 | Tempest |
| 2009/0142225 | A1 | 6/2009 | Tornqvist |
| 2009/0250407 | A1 | 8/2009 | Delano |
| 2009/0185959 | A1 | 9/2009 | Weber et al. |
| 2010/0219137 | A1 | 9/2010 | Lacasse |
| 2013/0193081 | A1 | 8/2013 | Vasiliu et al. |
| 2013/0341285 | A1 | 12/2013 | Marion |
| 2014/0027388 | A1 | 1/2014 | Constant |
| 2014/0263097 | A1 | 9/2014 | Lynn |
| 2016/0251243 | A1 | 9/2016 | Lynn |

* cited by examiner

SYSTEM FOR GENERATING AQUEOUS OZONE SOLUTION WITH VARIABLY CONTROLLED OZONE GENERATOR AND PIPE ASSEMBLY FOR IN-LINE MIXING

CROSS-REFERENCE TO RELATED APPLICATIONS

The present application is a Continuation-in-Part of U.S. application Ser. No. 17/862,506 filed Jul. 12, 2022 entitled WATER CIRCULATION SYSTEM WITH PIPE ASSEMBLY FOR IN-LINE MIXING TO CREATE AN OXIDATION REDUCTION POTENTIAL (ORP) IN WATER FOR A RECREATIONAL OR DECORATIVE WATER FEATURE which is a Continuation of U.S. application Ser. No. 17/722,613 filed Apr. 18, 2022 entitled WATER CIRCULATION SYSTEM WITH PIPE ASSEMBLY FOR IN-LINE MIXING TO CREATE AN OXIDATION REDUCTION POTENTIAL (ORP) IN WATER FOR A RECREATIONAL OR DECORATIVE WATER FEATURE which is a Continuation-in-Part of U.S. application Ser. No. 17/672,547 filed Feb. 15, 2022 entitled AIR SCRUBBER SYSTEM WITH PIPE ASSEMBLY FOR IN-LINE MIXING TO CREATE AN OXIDATION REDUCTION POTENTIAL (ORP) IN WATER which is a Continuation-in-Part of U.S. application Ser. No. 17/408,742 filed Aug. 23, 2021 entitled TRANSPORTABLE SYSTEM FOR CREATING AN OXIDATION REDUCTION POTENTIAL (ORP) IN WATER WITH PIPE ASSEMBLY FOR IN-LINE MIXING which is a Continuation-in-Part of U.S. application Ser. No. 17/168,911 filed Feb. 5, 2021 entitled SYSTEM FOR CREATING AN OXIDATION REDUCTION POTENTIAL (ORP) IN WATER WITH PIPE ASSEMBLY FOR IN-LINE MIXING which is a Continuation-in-Part of U.S. application Ser. No. 17/150,449 filed Jan. 15, 2021 entitled SYSTEM FOR CREATING AN OXIDATION REDUCTION POTENTIAL (ORP) IN WATER WITH MULTI-PATH MANIFOLD FOR MIXING AND DISTRIBUTION which is a Continuation-in-Part of U.S. application Ser. No. 17/078,799 filed Oct. 23, 2020 entitled SYSTEMS AND METHODS FOR CREATING AN OXIDATION REDUCTION POTENTIAL (ORP) IN WATER FOR PATHOGENIC CLEANSING AND/OR DEGREASING OF HARD SURFACES AND EQUIPMENT which is a Continuation of U.S. application Ser. No. 15/476,326 filed Mar. 31, 2017 entitled SYSTEMS AND METHODS FOR CREATING AN OXIDATION REDUCTION POTENTIAL (ORP) IN WATER FOR PATHOGENIC CLEANSING AND/OR DEGREASING OF HARD SURFACES AND EQUIPMENT which is a Continuation-in-Part of U.S. application Ser. No. 15/446,331 filed Mar. 1, 2017 entitled SYSTEMS AND METHODS FOR CREATING AN OXIDATION REDUCTION POTENTIAL (ORP) IN WATER FOR PATHOGENIC CONTROL WITH THE WATER AND OZONE SOLUTIONS THEREOF BEING SUPPLIED TO ONE OR MORE WASH-DOWN STATIONS which is a Continuation-in-Part of U.S. application Ser. No. 15/355,884 filed Nov. 18, 2016 entitled SYSTEMS AND METHODS FOR CREATING AN OXIDATION REDUCTION POTENTIAL (ORP) IN WATER FOR PATHOGENIC CONTROL which is a Continuation-in-Part of U.S. application Ser. No. 15/050,777 filed Feb. 23, 2016 entitled SYSTEMS AND METHODS FOR CREATING AN OXIDATION REDUCTION POTENTIAL (ORP) IN WATER FOR PATHOGENIC CONTROL which claims the benefit of U.S. Provisional Application Ser. No. 62/121,770 filed Feb. 27, 2015 entitled SYSTEMS AND METHODS FOR CREATING AN OXIDATION REDUCTION POTENTIAL (ORP) IN WATER FOR PATHOGENIC CONTROL, all of which are incorporated by reference.

TECHNICAL FIELD

The present disclosure relates to systems for generating aqueous ozone solution for pathogenic control.

BACKGROUND

Water intended for potable use (e.g., drinking water), may contain disease-causing organisms, or pathogens, which can originate from the source of the water, from resistance to water treatment techniques, from improper or ineffectual water treatment techniques, or so forth. Pathogens include various types of bacteria, viruses, protozoan parasites, and other organisms. To protect drinking water from disease-causing organisms, or pathogens, water suppliers often add a disinfectant, such as chlorine, to the water. However, disinfection practices can be ineffectual because certain microbial pathogens, such as *Cryptosporidium*, are highly resistant to traditional disinfection practices. Also, disinfectants themselves can react with naturally occurring materials in the water to form byproducts, such as trihalomethanes and haloacetic acids, which may pose health risks.

A major challenge for water suppliers is how to control and limit the risks from pathogens and disinfection byproducts. It is important to provide protection from pathogens while simultaneously minimizing health risks to the population from disinfection byproducts. Oxidation reduction potential (ORP) can be used for water system monitoring to reflect the antimicrobial potential of the water, without regard to the water quality, with the benefit of a single-value measure of the disinfection potential, showing the activity of the disinfectant rather than the applied dose.

There are a number of systems that generate ORP in water by injecting ozone into the water to create an ozone and water solution (sometimes referred to as an "aqueous ozone solution"). However, high pressure water applications present challenges, often requiring the use of an intermediate tank that must be filled prior to use (much like a water heater). To overcome such challenges, there is a need for improvements in the mixing and distribution of aqueous ozone solutions.

SUMMARY

Aspects of this disclosure are directed to a system for generating aqueous ozone solution using a variably controlled ozone generator (hereinafter "the ozone generator") and a pipe assembly for in-line mixing of ozone into water that is supplied to the system.

In embodiments, a relay is configured to selectively activate the ozone generator by supplying an electrical current to the ozone generator. The ozone generator is variably controlled through the use of a variable resistor that is configured to control the rate of ozone output from the ozone generator by adjusting the electrical current supplied to the ozone generator from the relay. The ozone generator is selectively activated by the relay through the use of a flow switch that is configured to transmit one or more control signals to the relay in response to sensing a flow of water, where the relay is then configured to supply the electrical current to the ozone generator in response to the one or more control signals.

The pipe assembly includes a first flow path for water to flow through. The first flow path includes one or more ozone intake ports that are fluidically coupled to the ozone generator. The pipe assembly further includes a second flow path fluidically coupled in parallel with the first flow path. The second flow path includes a control valve that selectively permits a portion of the water to flow through the second flow path to produce a negative pressure in the first flow path so that ozone is drawn into the first flow path through the one or more ozone intake ports and mixed into the water flowing through the first flow path to produce an aqueous ozone solution.

This Summary is provided solely as an introduction to subject matter that is fully described in the Detailed Description and Drawings. The Summary should not be considered to describe essential features nor be used to determine the scope of the Claims. Moreover, it is to be understood that both the foregoing Summary and the following Detailed Description are example and explanatory only and are not necessarily restrictive of the subject matter claimed.

BRIEF DESCRIPTION OF THE DRAWINGS

The Detailed Description is provided with reference to the accompanying Drawings. The use of the same reference numbers in different instances may indicate similar or identical items. The Drawings are not necessarily to scale, and embodiments provided in the Drawings may be modified or combined to arrive at different embodiments without departing from the scope of this disclosure. Furthermore, the steps/operations of any disclosed processes may be performed in an arbitrary order, unless otherwise specified herein. In the Drawings.

DETAILED DESCRIPTION

Reference will now be made in detail to the subject matter disclosed, which is illustrated in the accompanying drawings.

Embodiments of this disclosure are directed to systems for creating an oxidation reduction potential (ORP) in water using one or more pipe assemblies for in-line mixing of water and ozone to produce an aqueous ozone solution. In residential or commercial applications, the system may be configured to supply the aqueous ozone solution to one or more taps that receive water from a main water source (e.g., the main water line of a building). In this regard, the system can be employed as a whole home or building water cleansing, disinfecting, and/or softening solution. Alternatively, the system may be used for a particular zone of a residential or commercial building. In some cases, a plurality of systems can be used to ozonate water in a plurality of zones within a residential or commercial building. The system can also be used for cleansing and/or degreasing hard surfaces such as plastic, glass, ceramic, porcelain, stainless steel, or the like. The system can also be used for cleansing and/or degreasing equipment such as food service equipment which may include, but are not limited to, ovens, ranges, fryers, grills, steam cookers, oven stacks, refrigerators, coolers, holding cabinets, cold food tables, worktables, ice machines, faucets, beverage dispensing equipment, beer dispensers, shelving food displays, dish washing equipment, and grease traps. The system can also be used for cleansing and/or degreasing HVAC or plumbing systems such as roof top units, air scrubbers, humidifiers, water heaters, pumps, or the like.

An ORP value can be used for water system monitoring to reflect the antimicrobial potential of a given sample of water or ozone-enriched water (sometimes referred to herein as an "aqueous ozone solution"). ORP is measured in millivolts (mV), with typically no correction for solution temperature, where a positive voltage shows a solution attracting electrons (e.g., an oxidizing agent). For instance, chlorinated water will show a positive ORP value whereas sodium sulfite (a reducing agent) loses electrons and will show a negative ORP value. Similar to pH, ORP is not a measurement of concentration directly, but rather of activity level. In a solution of only one active component, ORP indicates concentration. The World Health Organization (WHO) adopted an ORP standard for drinking water disinfection of 650 millivolts. That is, the WHO stated that when the oxidation-reduction potential in a body of water measures 650 (about ⅔ of a volt), the sanitizer in the water is active enough to destroy harmful organisms almost instantaneously. For example, *E. coli, Salmonella, Listeria*, and Staph pathogens have survival times of under 30 seconds when the ORP is above 650 mV, compared against >300 seconds when it is below 485 mV.

An example ORP sensor uses a small platinum surface to accumulate charge without reacting chemically. That charge is measured relative to the solution, so the solution "ground" voltage comes from the reference junction. For example, an ORP probe can be considered a millivolt meter, measuring the voltage across a circuit formed by a reference electrode constructed of silver wire (in effect, the negative pole of the circuit), and a measuring electrode constructed of a platinum band (the positive pole), with the water in-between.

Increasingly, microbial issues are commanding the attention of water treatment operators, regulators, media, and consumers. There are many treatment options to eliminate pathogenic microbes from drinking water. One such option includes ozone ($O_3$), an oxidizing agent approved for drinking water treatment by the U.S. Environmental Protection Agency. Ozone is one of the strongest disinfectants approved for potable water treatment capable of inactivating bacteria, viruses, *Giardia*, and *Cryptosporidium*.

The disclosed system may be configured to output water having an ORP of about 600 mV to about 1000 mV, with particular embodiments being configured to output water having an ORP of about 700 mV to about 900 mV to provide pathogenic control. Additionally, the system may be configured to reduce the surface tension of the water being used to cleanse and/or degrease hard surfaces and equipment by creating an aqueous ozone solution wherein the surface tension of the water is reduced from about 72 Millinewtons per meter at 20 degrees Centigrade to about 48-58 Millinewtons per meter at 20 degrees Centigrade to greatly improve the cleansing and/or degreasing qualities thereof.

In embodiments, the system employs at least one pipe assembly for in-line mixing of water and ozone. Through the use of a pipe assembly that is structurally separate from an ozone generator and its ancillary electronics, the system is able to handle high pressure water flow through the pipe assembly without fear of a leak causing damage to electronic components associated with the ozone generator (e.g., power distribution circuits, relays, transformers, etc.). Furthermore, the pipe assembly may be linearly disposed within the water supply framework of a residential/commercial building for improved throughput with a reduced footprint.

Figure 1:
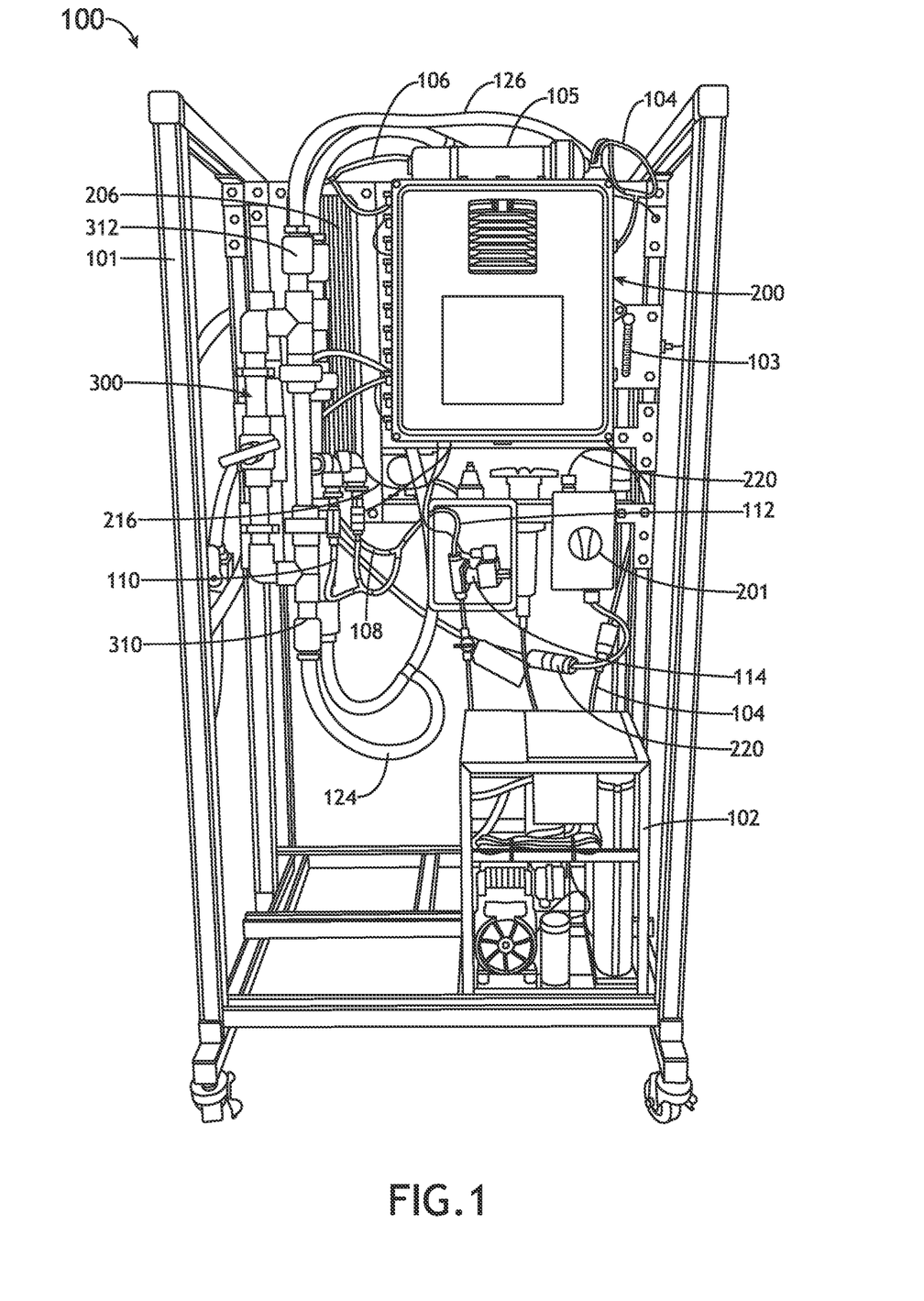
FIG. 1 is a front view of a system for generating aqueous ozone solution, in accordance with one or more embodiments of this disclosure.

FIG. 1 illustrates a system 100 for creating an ORP in water by mixing ozone into the water. The output water is ozone-enriched water (sometimes referred to herein as the "aqueous ozone solution"). The system 100 includes a variably controlled ozone generator 206 (hereinafter "the ozone generator 206") configured to output ozone for creating an ORP in water and a pipe assembly 300 for in-line mixing of the ozone into the water in order to output an aqueous ozone solution. Although the system 100 is discussed with regard to applications that employ water to generate an aqueous ozone solution, it is contemplated that the system 100 may be configured to generate other types of ozonated fluid solutions for the purposes of cleansing, degreasing, decontaminating, and/or fluid treatment.

Figure 2:
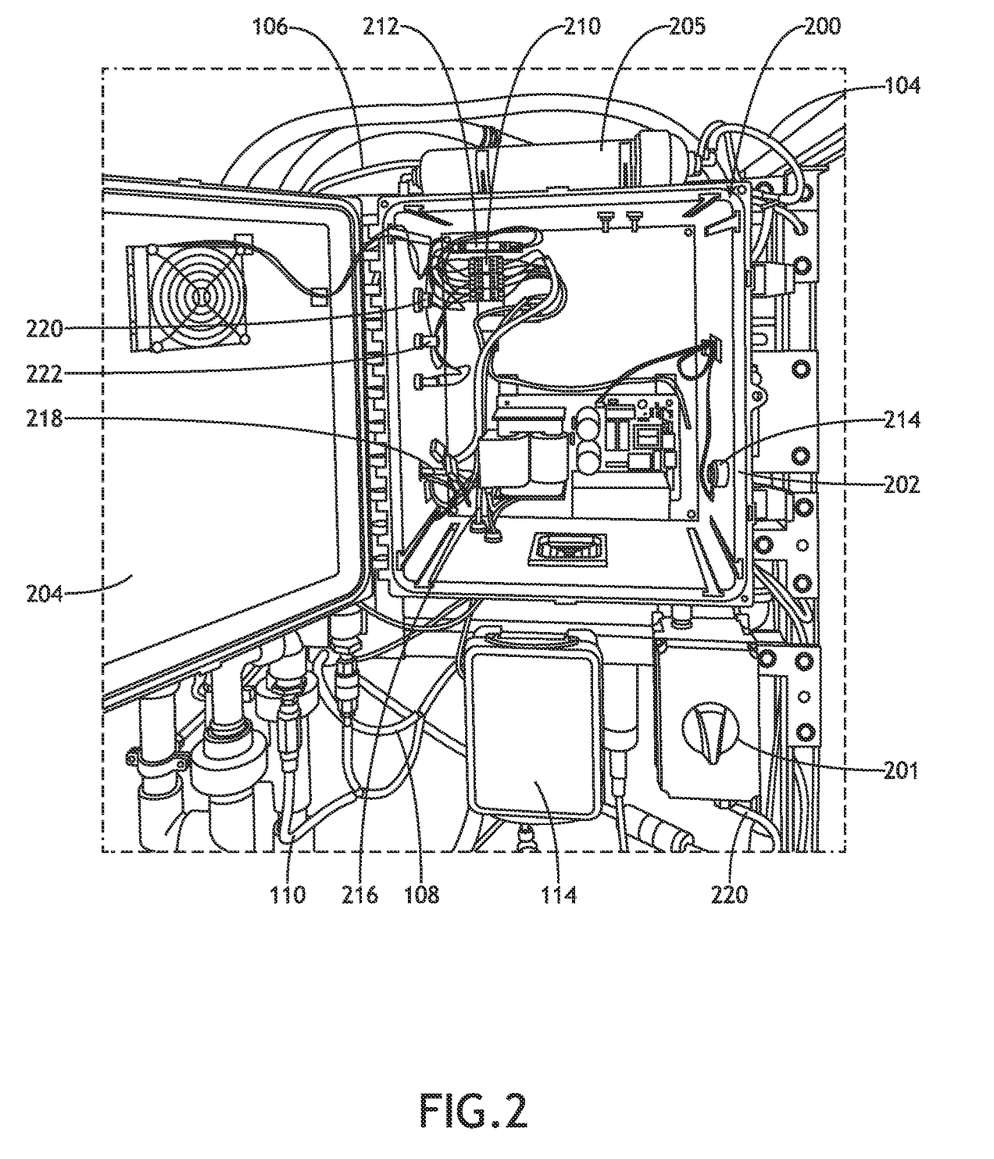
FIG. 2 is a perspective view of an open control box of the system for generating aqueous ozone solution, in accordance with one or more embodiments of this disclosure.

As shown in FIG. 1, the ozone generator 206 may be communicatively coupled to a control box 200 that contains electronic circuits and components for controlling the ozone generator 206 and other devices within the system 100. In embodiments, the ozone generator 206, the control box 200, and the pipe assembly 300 are independently locatable, separate structures. As shown in FIG. 2, the control box 200 may comprise an enclosure 202 with a securable lid/cover 204 that can enclose (e.g., when secured/closed) and provide access to (e.g., when removed/opened) the components housed in an interior portion of the control box 200. In some embodiments, the securable lid/cover 204 may be secured to the enclosure 202 by a hinge on one side and a latch or fastener on an opposing side. In other embodiments, the securable lid/cover 204 may be a sliding cover or may be secured to the enclosure 202 by one or more fasteners (e.g., screws to mate with bores in the enclosure 202, latches, interference fit fasteners, clipping fasteners, magnetic fasteners, or the like). The enclosure 202 may further include coupling portions to couple with a power source (e.g., power cable 220), a switch to engage or disengage power to the system 100, an indicator 222 (e.g., a light source), any combination thereof, and so forth.

The control box 200 may be communicatively coupled to the ozone generator 206 by one or more connectors 216 (e.g., wires, cables, etc.) for supplying an electrical current to the ozone generator 206 by transmitting a power signal from the control box 200 to the ozone generator 206. In embodiments, the ozone generator 206 may include a corona discharge tube configured to use oxygen to generate ozone, such as through splitting of oxygen molecules in the air through electrical discharge caused by supplying power to a dielectric material within the corona discharge tube. The ozone generator 206 may be powered by a power supply unit 212 (e.g., a 120V/240V power supply unit). A power signal from power supply unit 212 may be transmitted to the ozone generator 206 by a relay 210 that is coupled to the power supply unit 212. The ozone generator 206 is variably controlled through the use of a variable resistor 214 (e.g., a rheostat or potentiometer) that is configured to control the rate of ozone output from the ozone generator 206 by adjusting (e.g., increasing/decreasing) the electrical current supplied to the ozone generator 206 from the relay 210.

In some embodiments, the control box 200 further includes a transformer 208 communicatively coupled in between the relay 210 and the ozone generator 206. The power signal may be transformed via the transformer 208 by stepping up/down the voltage of the power signal to apply a suitable voltage for the dielectric within the corona discharge tube of the ozone generator 206.

The relay 210 may comprise a switchboard with analog or digital logic circuits. For example, the relay 210 may include a processor, microcontroller, or other programmable logic device, or a circuit formed from discrete logic devices, or any combination of the foregoing elements. The relay 210 is configured to control distribution of power and/or communication signals within the control box 200 and between the control box 200 and other system components (e.g., ozone generator 206, sensors, etc.). For example, the relay 210 may be connected to power supply unit 212, ozone generator 206, and any sensors/switches (e.g., flow switch 322) of the system 100. In embodiments, the relay 210 is configured to selectively activate (i.e., turn on) the ozone generator 206 by supplying an electrical current to the ozone generator 206 in response to one or more control signals received at the relay 210. For example, the ozone generator 206 may be selectively activated by the relay 210 through the use of a flow switch 322 that is configured to transmit one or more control signals to the relay 210 in response to sensing a flow of water, where the relay 210 is then configured to supply the electrical current to the ozone generator 206 in response to receiving the one or more control signals from the flow switch 322.

The ozone generator 206 may be configured to produce from about 500 mg ozone per hour to about 5000 mg ozone per hour, although other ranges may be appropriate depending on the application. In some embodiments, the ozone generator 206 may include other methods and systems for generating ozone, including but not limited to, electrochemical cells configured to generate ozone from water by placing an anode and a cathode in contact with opposite sides of a proton exchange membrane (PEM), and supplying power to the cell, whereby water flowing over the surface of the anode breaks down into hydrogen atoms and oxygen atoms that assemble to form $O_3$ (ozone).

The system 100 may further include an air dryer 105 (or filter), which may be externally coupled to the control box 200. The air dryer 105 is configured to remove moisture from air before the air is supplied to the ozone generator 206. The air dryer 105 may be configured to dry the air to a minus dew point by removing water vapor or moisture therefrom, where the water could inhibit the production of ozone by the ozone generator 206.

In some embodiments, the air dryer 105 includes or is coupled to an air compressor. The pressure provided by the compressor can vary depending on the water pressure supplied to the system 100, where the pressure applied by the compressor can be balanced based on the flow rate of air received by the ozone generator 206 and the water pressure supplied to the system 100 to obtain a particular ORP of the water. For example, the compressor may be configured to compress the filtered air at least about 15 KPa (e.g., more particularly at a pressure of 18 KPa or about 2.6 psi) to provide a gas throughput in the ozone generator 206 of about 8 SCFH (standard cubic feet per hour), where the water pressure in each fluid path is about 25 psi to 100 psi (e.g., a reasonable rating for many residential and commercial facilities), to provide an ORP in the water at the water output port of at least about 600 mV (e.g., about 600 mV to about 1000 mV, more particularly about 700 to 900 mV). At these pressures, the ozone generator 206 has a residence time of the gas of about three seconds. The pressure applied by the compressor can affect the rate at which the gas flows through an ozone generator 206, which can affect contact time of the air with the components of the ozone generator 206, which can also affect mass gas transfer rates within the ozone generator 206.

In some embodiments, the control box 200 also includes a vent (e.g., an exhaust vent) to bring cool air into the enclosure 202 and/or remove hot air from the enclosure 202. The vent may be equipped with a fan to further facilitate airflow.

Figure 7:
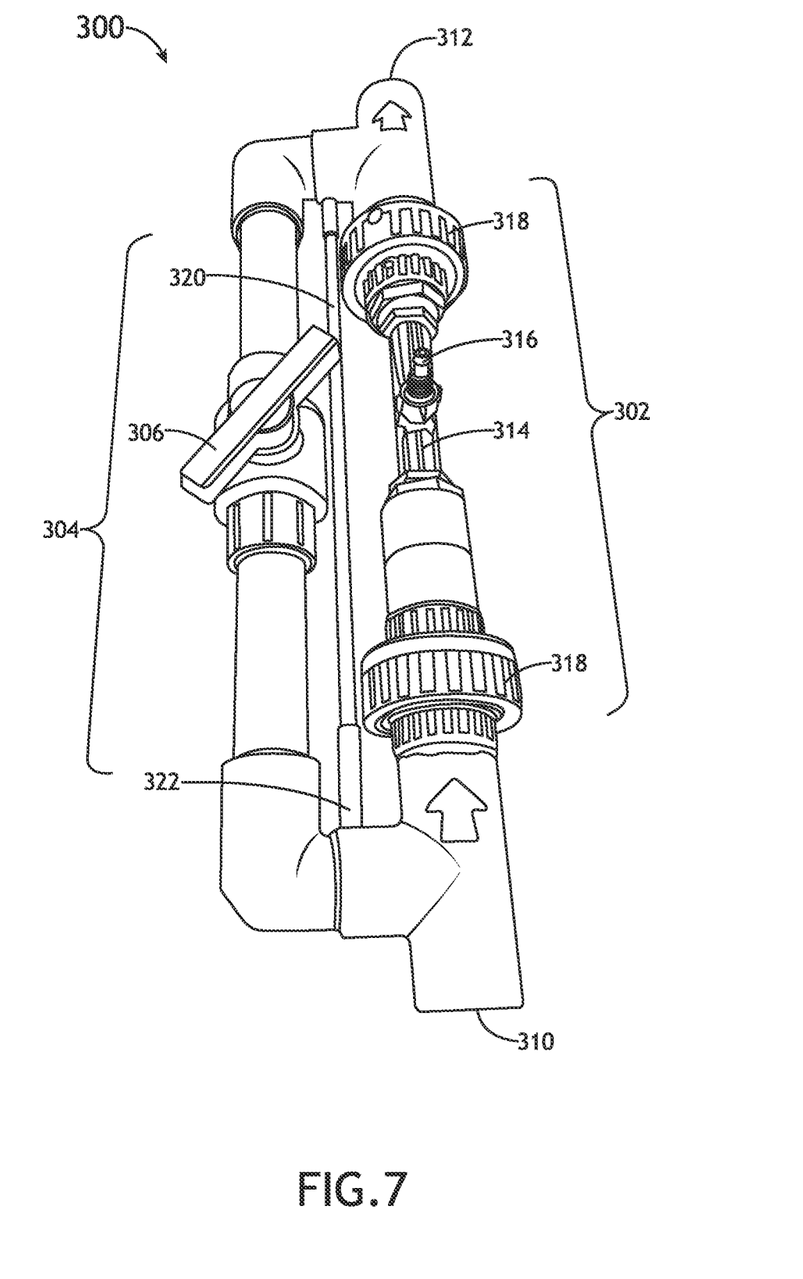
FIG. 7 is a perspective view of a pipe assembly of the system for generating aqueous ozone solution, in accordance with one or more embodiments of this disclosure.
Figure 8A:
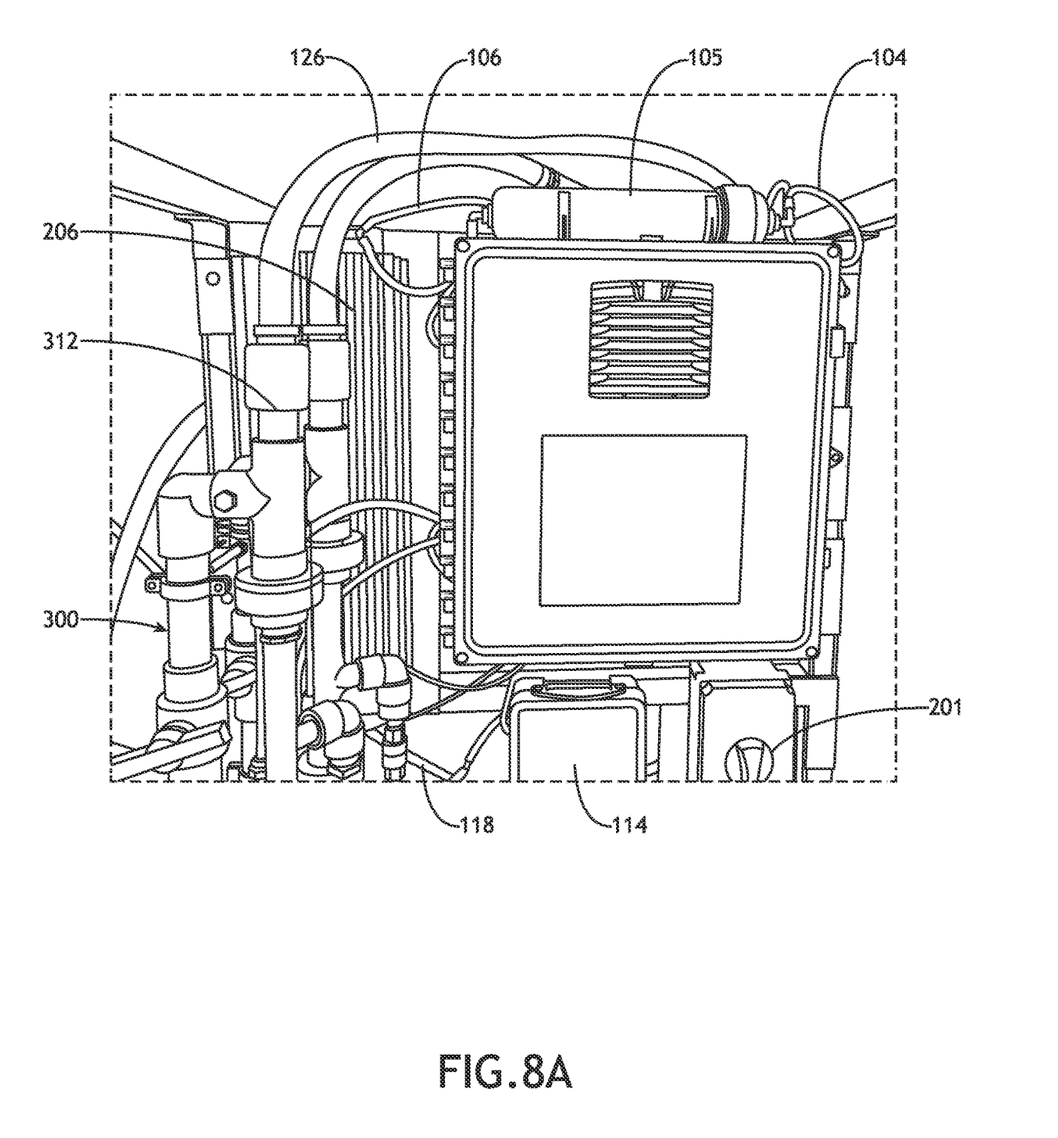
FIG. 8A is a partial front view of an upper portion of the system for generating aqueous ozone solution, in accordance with one or more embodiments of this disclosure.
Figure 8B:
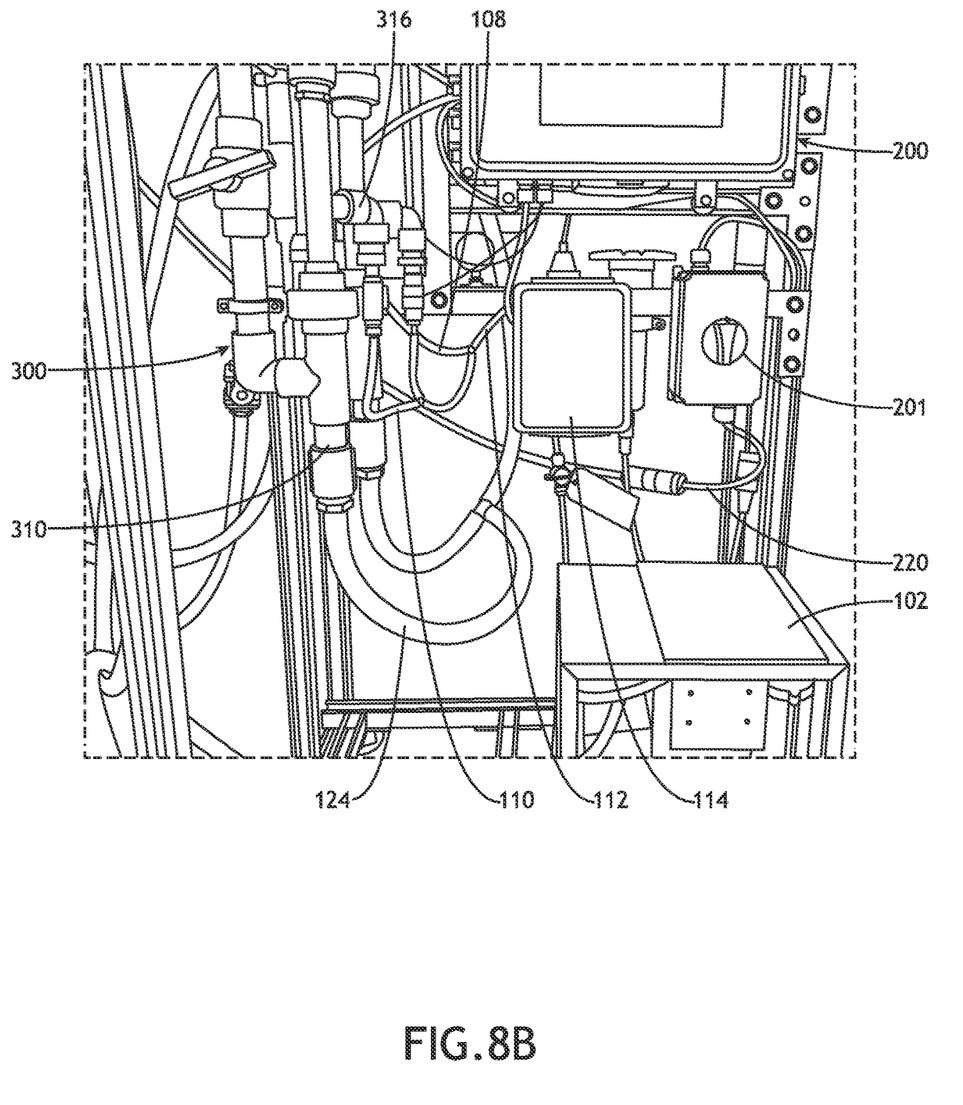
FIG. 8B is a partial front view of a lower portion of the system for generating aqueous ozone solution, in accordance with one or more embodiments of this disclosure.

FIG. 7 illustrates the pipe assembly 300, in accordance with one or more embodiments of this disclosure. As shown in FIG. 7, the pipe assembly 300 includes a first flow path 302 for water to flow through. The first flow path 302 may include one or more pipe segments and/or fittings that define a first fluid pathway between a water input port 310 and a water output port 312 of the pipe assembly 300. The first flow path 302 includes one or more ozone intake ports 316 that are fluidically coupled to the ozone generator 206. In embodiments, one or more ozone intake ports 316 of the pipe assembly 300 are fluidically coupled to the ozone generator 206 by one or more tubes 108, 110 (e.g., flexible tubing, pipes, etc.) for transferring ozone from the ozone generator 206 to the pipe assembly 300. For example, see FIGS. 1 and 8B.

As shown in FIG. 1, in some embodiments, the system 100 may further include a solenoid valve 114 configured to purge residual ozone from the one or more tubes 108, 110 in between uses (e.g., when the system 100 starts up, shuts down, or transitions between active/inactive modes). For example, the solenoid valve 114 may be configured to receive a control signal from the relay 210 to indicate startup, shutdown, and/or ozone generator activity/inactivity, wherein the control signal triggers the solenoid valve to purge any leftover ozone from the one or more tubes 108, 110. This avoids excessive ozone in the tubes 108, 110 when the ozone generator 206 is activated, as the presence of too much ozone in the tubes 108, 110 may cause an unsafe condition, such as a fire/explosion, component damage, or ozone leak. In some embodiments, the solenoid valve 114 is fluidically coupled to tubes 108, 110 by one or more tubes 112 (e.g., flexible tubing, pipes, etc.). Alternatively, the solenoid valve 114 may be directly coupled to tube(s) 108 or tube(s) 110.

Referring again to FIG. 7, the pipe assembly 300 further includes a second flow path 304 fluidically coupled in parallel with the first flow path 302. For example, the second flow path 304 includes one or more pipe segments and/or fittings that define a second fluid pathway in parallel with the first fluid pathway (first flow path 302) between the water input port 310 and the water output port 312 of the pipe assembly 300. The second flow path 304 may form a D or P shaped branch out of the first flow path 302. This structural arrangement may help maintain more water flow through the first flow path 302 than the second flow path 304.

The second flow path 304 includes a control valve 306 that is configured to selectively permit (or restrict) water flow through the second flow path 304. When the control valve 306 is opened to permit a portion of the water to flow through the second flow path 304, the fluid action produces a negative pressure in the first flow path 302. The negative pressure then causes ozone from the ozone generator 206 to be drawn into the first flow path 302 through the one or more ozone intake ports 316 and mixed into the water flowing through the first flow path 302. In some embodiments, the control valve 306 is adjustable to vary the negative pressure produced in the first flow path 302 in order to control an ozone concentration of the aqueous ozone solution output by the system 100. For example, the control valve 306 may be adjustable to control the flow rate of water through the second flow path 304 in order to increase/decrease suction through the one or more ozone intake ports 316. In some embodiments, the level of suction (and hence the ozone concentration of the resulting aqueous ozone solution) can be increased by increasing the flow rate of water through the second flow path 304; and similarly, the level of suction (and hence the ozone concentration of the resulting aqueous ozone solution) may be reduced by decreasing the flow rate of water through the second flow path 304. Some configurations may be reversed such that the level of suction (and hence the ozone concentration of the resulting aqueous ozone solution) can be increased by decreasing the flow rate of water through the second flow path 304, and the level of suction (and hence the ozone concentration of the resulting aqueous ozone solution) may be reduced by increasing the flow rate of water through the second flow path 304.

In embodiments, the first flow path 302 includes fluid mixer 314 that is coupled to or integrated within the first flow path 302. For example, the fluid mixer 314 may be removably coupled between two pipe fittings 318 to allow for easy removal or replacement of the fluid mixer 314 if needed. The fluid mixer 314 may be configured to introduce/inject ozone generated by the ozone generator 206 into the water flowing through the first flow path 302. For example, the fluid mixer 314 may be fluidically coupled to the ozone intake port 316 and configured to inject at least a portion of the ozone received via the ozone intake port 316 into the water flowing through the first flow path 302.

The fluid mixer 314 may be a multi-port coupler including a water inlet, a water outlet, and an ozone input port (e.g., ozone intake port 316). The multi-port coupler may simply be pipe/tube fittings with an ozone input port (e.g., ozone intake port 316) formed therein, 3-way pipe/tube fittings, or the like.

In some embodiments, the multi-port coupler includes a venturi. A venturi can include an injector venturi design (e.g., a "T" design), where the venturi is coupled between the water inlet and the water outlet, and where ozone is introduced to the venturi through another port (i.e., the ozone input port) positioned perpendicular to the flow path of the water (from the water inlet to the water outlet). During operation, ozone generated by the ozone generator 206 is drawn into the venturi and mixed with the water stream flowing from the water inlet to the water outlet. A pressure differential between the water inlet and the water outlet may serve to facilitate drawing the ozone into the venturi and to facilitate mixing of the ozone and the water. In some embodiments, a pressure differential greater than 20 psi inlet over outlet (e.g., at least a 20 psi difference between the water inlet and the water outlet, with pressure higher at the water inlet) is provided to generate negative suction in the venturi to thereby draw in the generated ozone, while assuring the energy for water flow and pressure for operation of the venturi.

In order to further increase effectiveness of the mixing process delivered by the venturi, the aqueous ozone solution may pass through an in-line mixer coupled between the venturi and the water outlet. In this regard, the fluid mixer 314 may include a combination of a venture and an in-line mixer, or another type of multi-port coupler with an in-line mixer. The in-line mixer can facilitate further breaking or mixing of ozone bubbles already introduced to the water to generate a mixture (or solution) of water and substantially uniform-sized ozone bubbles. The small uniform-size ozone bubbles can adhere to each other to lower the surface tension of the aqueous ozone solution. For example, water can have a surface tension of about 72 Millinewtons, whereas the solution of water and substantially uniform-sized ozone bubbles can have a surface tension of about 48-58 Millinewtons. In embodiments, the in-line mixer has an internal diameter that equals an internal diameter of the output port of the venturi to which the in-line mixer is coupled. The same internal diameter can provide an uninterrupted transition of the fluid flowing from the venturi to the in-line mixer, such as to maintain a vortex action or mixing action of the water and the ozone bubbles. The in-line mixer also provides increased contact time between the water and ozone bubbles and can facilitate preparation of uniform ozone bubble size. In some embodiments, the in-line mixer has a length of about two inches downstream from the venturi, which can allow sufficient time for the velocity of the vortex action caused by the pressure differential of the venturi to crush the gaseous bubbles entrained in the solution into uniformed size bubbles. The in-line mixer can also reintroduce undissolved gas back into the solution resulting in increased efficiency as well as reduced off-gas at the point of application. The in-line mixer can include multiple chambers through which the aqueous ozone solution flows. The size of the chambers can be determined based on the water flow (e.g., throughput), gas mixing, and desired time exposure. In some embodiments, operation of the system 100 produces a water stream at the water output port having a molar concentration of ozone of at least 20%, or more particularly at least 25%, far surpassing previous systems that have mass gas transfer rates of less than 10%.

Figure 6:
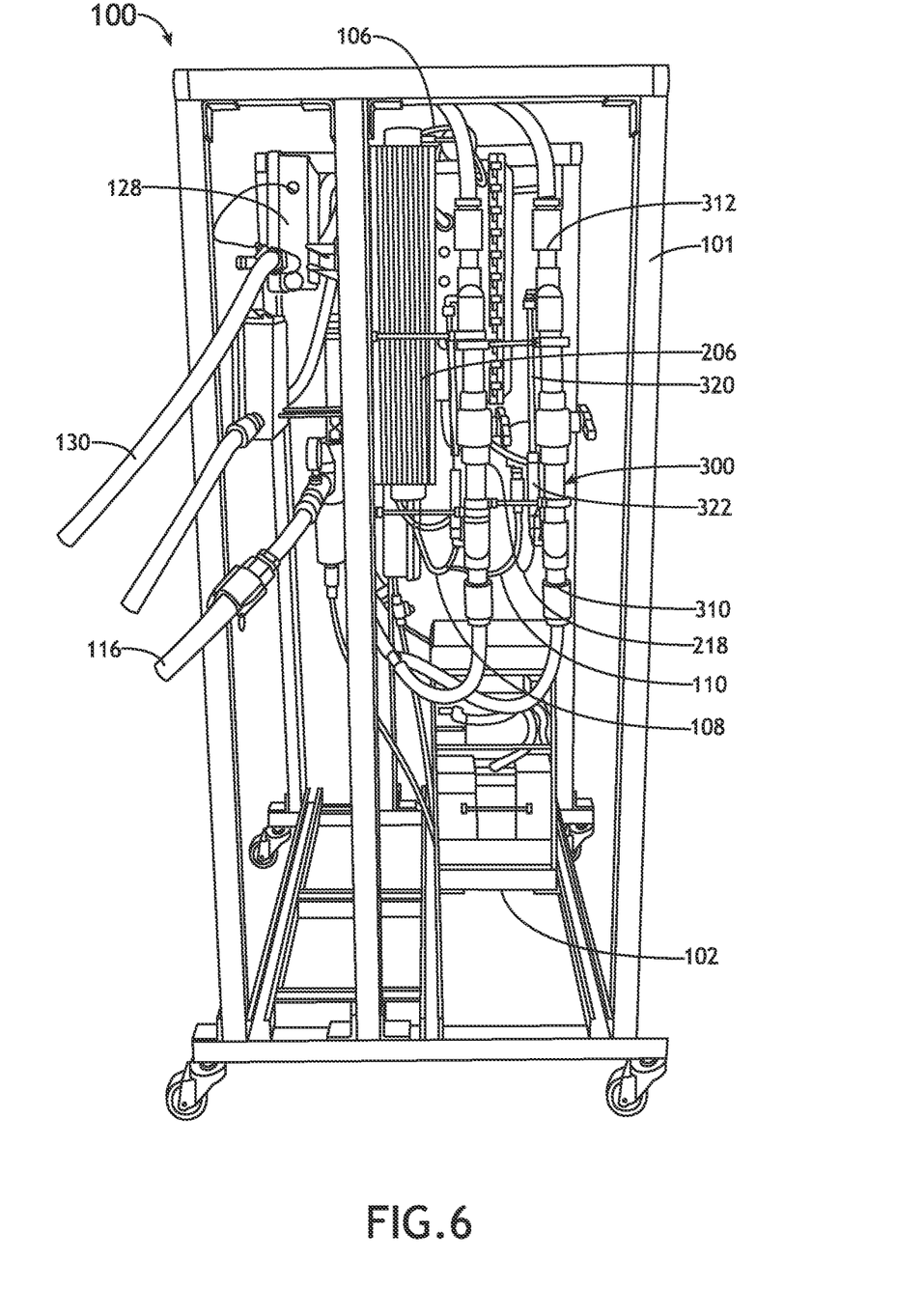
FIG. 6 is a left side view of the system for generating aqueous ozone solution, in accordance with one or more embodiments of this disclosure.

The control box 200 is communicatively coupled to a flow switch 322 configured to detect water flow through the system 100. As shown in FIGS. 6 and 7, the flow switch 322 may be integrated within or coupled to the pipe assembly 300. For example, the flow switch 322 may be fluidically coupled to a third flow path 320 that is in parallel with the first and second flow paths 302 and 304 of the pipe assembly 300. In other embodiments, the flow switch 322 may be coupled to any other the fluid path for water flow through the system 100 (e.g., input line 124, output line 126, flow path 302, flow path 304, etc.).

The flow switch 322 can be configured to provide electric signals indicative of water flow through the system 100 (e.g., by sensing flow through flow path 320, or another fluid pathway in alternative embodiments). For example, the flow switch 322 may be a mechanical flow switch/sensor, electromagnetic flow switch/sensor, pressure-based flow switch/sensor, optical flow switch/sensor, or the like, configured to provide an electric signal indicative of a flow of fluid (e.g., water) through the system 100. In some embodiments, the flow switch 322 may be a solenoid-based flow switch/sensor, such as to avoid significant restriction of flow through the system 100.

Figure 4:
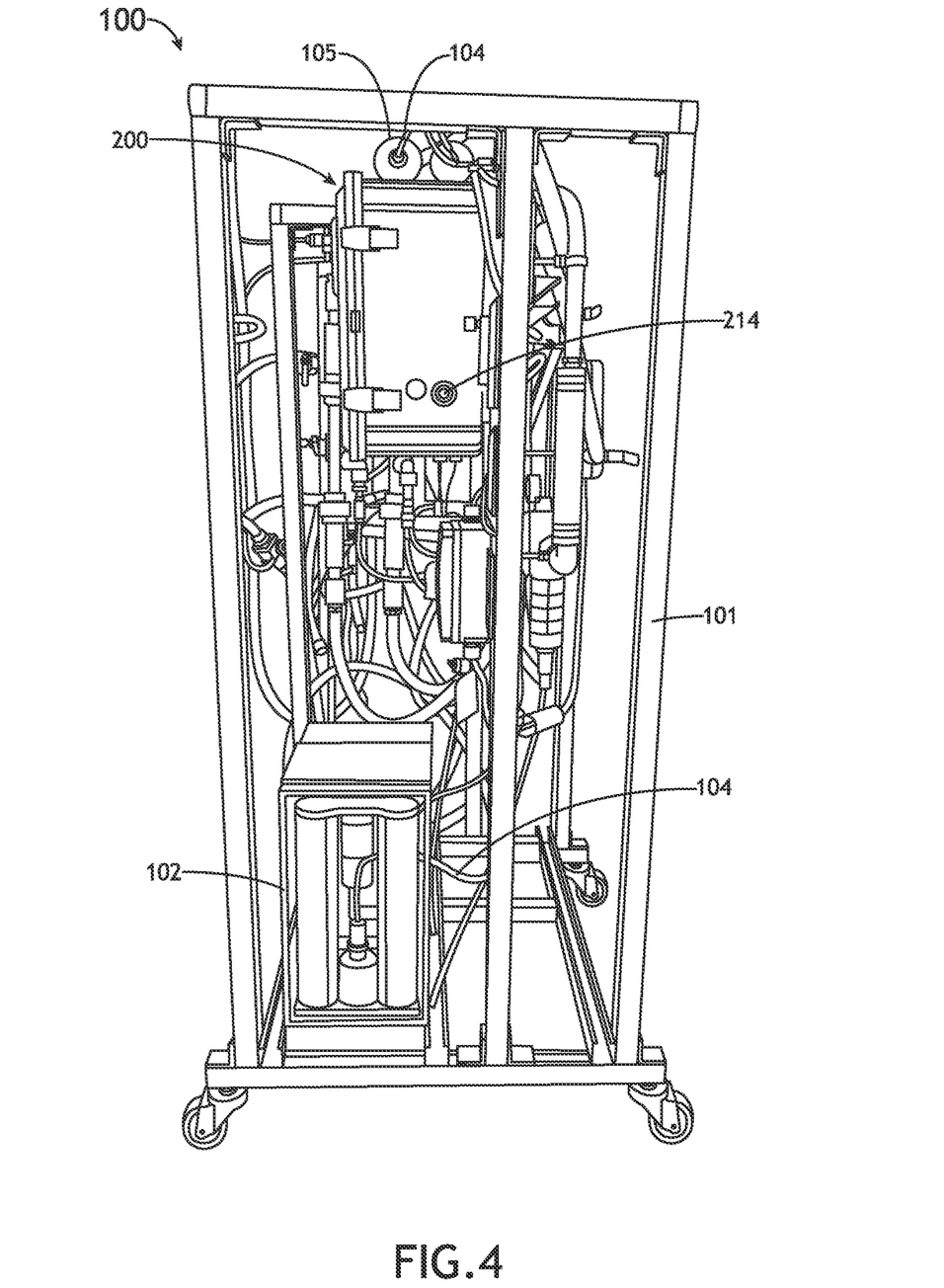
FIG. 4 is a right side view of the system for generating aqueous ozone solution, in accordance with one or more embodiments of this disclosure.

In embodiments, the flow switch 322 is configured to transmit one or more control signals to the relay 210 in response to sensing a flow of water through the system 100 (e.g., by sensing flow through flow path 320, or another fluid pathway in alternative embodiments). In response to receiving the one or more control signals, the relay 210 is configured to cause the ozone generator 206 to generate ozone. In some embodiments, after receiving the one or more control signals from the flow switch 322, the relay 210 transmits a power signal (thereby supplying an electrical current) to the ozone generator 206. This power signal may pass through one or more transformers 208 that step-up/step-down the voltage of the power signal. Between the relay 210 and the ozone generator 206, there is also the variable resistor 214 that is configured to adjust (e.g., increase/decrease) the electrical current supplied to the ozone generator 206 in order to control the rate of ozone output from the ozone generator 206. As shown in FIG. 4, the variable resistor 214 may be configurable via a knob or dial on an exterior of the control box 200. In other embodiments, the variable resistor 214 can be configured using a digital input device (e.g., switches, buttons, touch pad, touchscreen, etc.).

The system 100 allows for the ozone concentration to be controlled at two stages: (1) by adjusting the variable resistor 214 to control the output rate of the ozone generator 206; and (2) by adjusting the control valve to 306 to control the rate at which the ozone is mixed into the water that is flowing through the pipe assembly 300.

Figure 3:
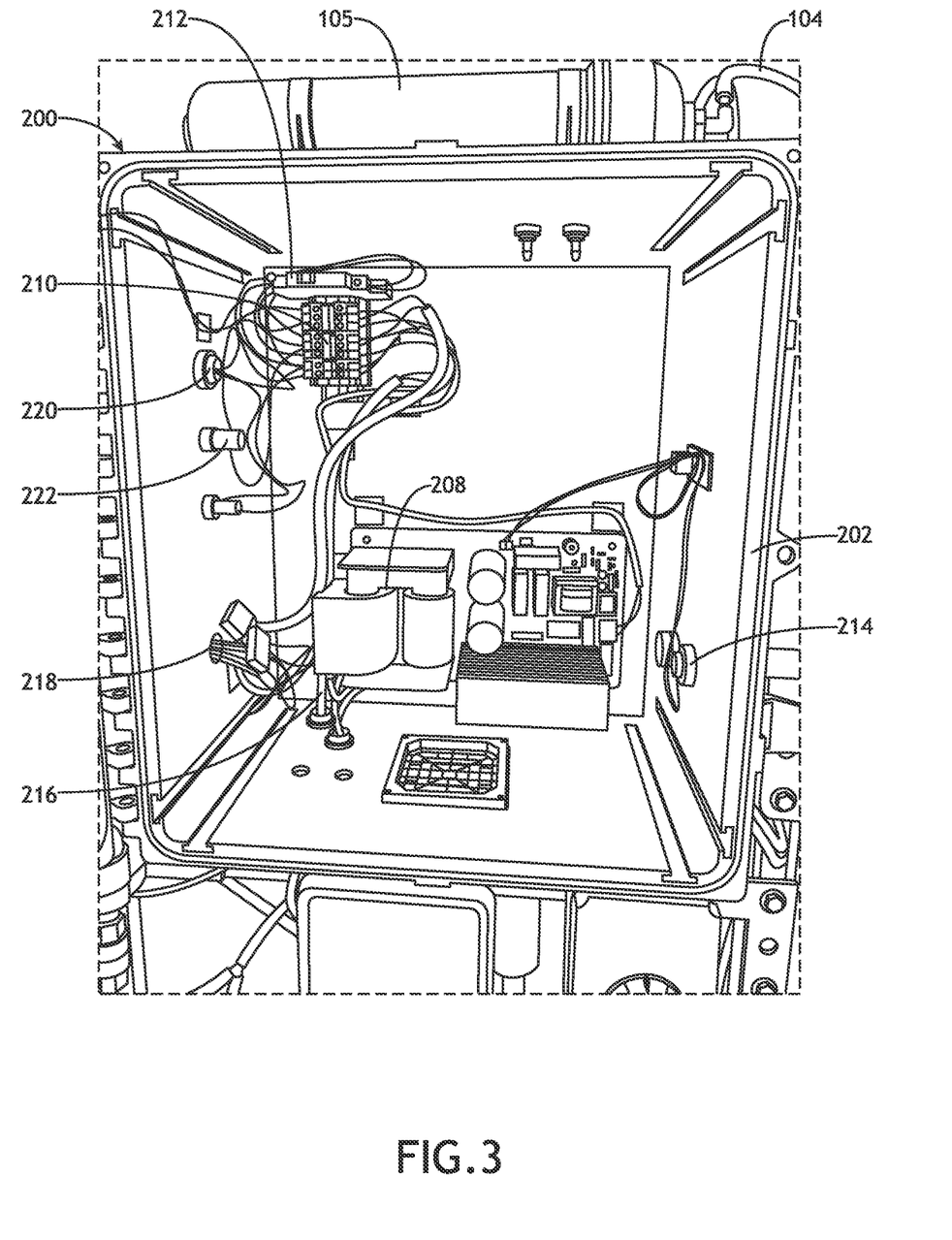
FIG. 3 is a zoomed-in view of the open control box of the system for generating aqueous ozone solution, in accordance with one or more embodiments of this disclosure.

The flow switch 322 may be communicatively coupled to the relay 210 by one or more connectors 218 (e.g., wires, cables, optical fibers, etc.) for transmitting signals between the flow switch 322 and the relay 210. For example, as shown in FIGS. 6 and 3, the one or more connectors 218 may be coupled to the relay 210 the enclosure 202. In other embodiments, the control box 200 may include a wireless communication interface (e.g., wireless receivers, transmitters, and/or transceivers) for receiving signals from the flow switch 322.

In some embodiments, the system 100 includes multiple flow switches 322 to provide redundancy and/or status indications for monitored fluid paths in order to detect faults (e.g., a faulty sensor, a clogged or disconnected fluid path, or the like). In some embodiments, the ozone generator 206 may be shut off when a fault is detected.

Although FIG. 7 illustrates pipe assembly 300, it is understood that any other pipe assembly 300 in the system 100 may be identically or similarly structured. In this regard, any components or configurations described with regard to pipe assembly 300 are applicable to all of the pipe assemblies 300 in the system 100. The system 100 may include one pipe assembly or a plurality of pipe assemblies. For example, FIGS. 1 through 6 illustrate an embodiment of the system 100 that includes two pipe assemblies 300, where both of the pipe assemblies 300 are coupled to the same water inlet 116, both of the pipe assemblies 300 are coupled to the ozone generator 206, and where the pipe assemblies 300 are coupled to separate output lines 126. In other embodiments, the system 100 may include a single pipe assembly 300 coupled to a single output line 126; or more than two pipe assemblies 300. If multiple pipe assemblies 300 are present, the pipe assemblies 300 can have shared/separate water input paths, shared/separate aqueous ozone solution output paths, shared/separate control boxes 200, and may share an ozone generator 206 or each pipe assembly 300 may have its own. The system 100 can also include any number of ozone generators 206. For example, each pipe assembly 300 (if there are more than one) may have its own ozone generator 206, or in some embodiments, two or more ozone generators 206 may be connected in parallel/series to the same pipe assembly 300 or set of pipe assemblies 300.

Referring again to FIG. 1, the system 100 may further include one or more oxygen concentrators 102 configured to supply oxygen-enriched air to the ozone generator 206. In embodiments, the oxygen concentrator 102 is configured to direct the oxygen-enriched air through the air dryer 105. The oxygen concentrator 102 may also remove moisture from the air. In this regard, the incoming air may undergo two drying stages. The oxygen concentrator 102 may be fluidically coupled to the air dryer 105 by one or more tubes 104 (e.g., flexible tubing, pipes, etc.) for transferring oxygen-enriched air from the oxygen concentrator 102 to the air dryer 105. The air dryer 105 may be fluidically coupled to the ozone generator 206 by one or more tubes 106 (e.g., flexible tubing, pipes, etc.) for transferring oxygen-enriched air from the air dryer 105 to the ozone generator 206. It should be understood that the oxygen concentrator 102 and the air dryer 105 are both optional components, but they are preferably included in the system 100. In some embodiments, the oxygen concentrator 102 is also coupled via the one or more tubes 104 to a pressure gauge and control valve 103 for adjusting the flow rate of oxygen-enriched air from the oxygen concentrator 102 to the air dryer 105, or directly to the ozone generator 206.

The system 100 may include a transportable support frame 101 configured to support various components of the system 100 (e.g., the ozone concentrator 102, control box 200, ozone generator 206, pipe assembly 300, and various electronics and fluid paths). For example, the control box 200, ozone generator 206, and the pipe assembly 300 may be mounted to the transportable support frame 101 by any combination of fasteners (e.g., screws, bolts, hooks, straps, etc.), brackets, and the like. The transportable support frame 101 may be a wheeled frame capable of transporting the system 100 from one place to another. For example, the transportable support frame 101 may be supported by a plurality of wheels, casters, or the like.

In some embodiments, the system 100 includes a main power switch 201 configured to connect or disconnect power to all of the system components. The main power switch 201 may be mounted to the transportable support frame 101. As shown in FIGS. 1 through 3, the main power switch 201 may be coupled to the power supply unit 212 of the control box 200 via one or more power cables 220.

Figure 5:
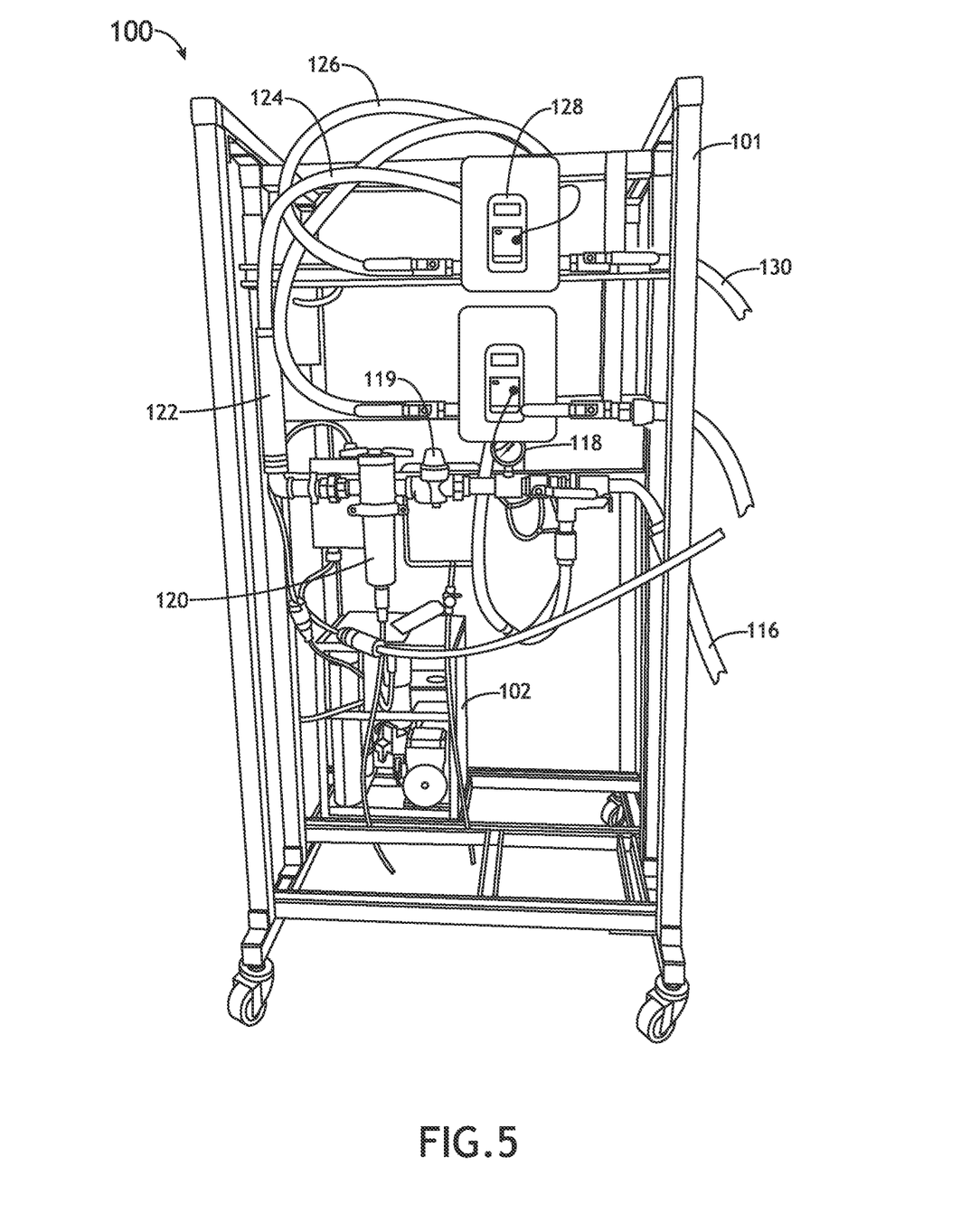
FIG. 5 is a rear view of the system for generating aqueous ozone solution, in accordance with one or more embodiments of this disclosure.

Referring now to FIG. 5, a backside of the transportable support frame 101 may support fluid paths for connecting the system 100 to an input (e.g., a water source) and an output (e.g., equipment). For example, an input path may include, but is not limited to, an inlet 116, a pressure gauge 118, a pressure regulator 119, a flow rate indicator 122, and one or more input lines 124 for directing the water into the pipe assembly 300. In embodiments, the input path may further include a sediment filter 120 configured to remove solids from the input water. In some embodiments, the sediment filter 120 may be configured to dispose of the solids through a waste tube. An output path may include, but is not limited to, one or more output lines 126 for directing aqueous ozone solution out of pipe assembly 300, one or more ORP sensors 128, and outlet 130.

In embodiments, the system 100 may further include one or more ORP monitors configured to detect an ORP of the water flowing through the plurality of fluid paths. For example, as shown in FIG. 5, the system 100 may include an ORP sensor 128 for detecting an ORP of the aqueous ozone solution being dispensed from an outlet 130 of the system 100.

In some embodiments, the ozone generator 206 is configured to supply ozone to the pipe assembly 300 at a rate of about 5 to 10 liters/min. In turn, the system 100 may be configured to dispense aqueous ozone solution at a rate of about 5 to 10 gal/min and can treat water having inlet pressures of between 50 psi and 100 psi to provide water having an ORP of between 600 mV and 1000 mV to provide pathogenic control without introduction of harsh treatment chemicals, such as chlorine. After operation of the system 100, the output aqueous ozone solution can provide removal of organic and inorganic compounds, can provide removal of micro-pollutants (e.g., pesticides), can provide enhancement of the flocculation/coagulation decantation process, can provide enhanced disinfection while reducing disinfection by-products, can provide odor and taste elimination of the treated water, and so forth. The solubility of ozone in water is quite good, about 10 to 15 times greater than for oxygen under normal drinking water treatment conditions. About 0.1 to 0.6 liters of ozone will dissolve in one liter of water. The size of the ozone gas bubble in the system 100 can influence gas transfer characteristics. In some embodiments, the fluid mixer 314 generates an ozone bubble size of about 2 to about 3 microns. For instance, micro-bubbles can be produced fluid mixer 314 and/or sheared into uniformed micro-size bubbles as the solution passes through flow path 302.

Corona discharge ozone can be used virtually anywhere, such as with portable versions of the system 100. Since ozone is made on site, as needed and where needed, there is no need to ship, store, handle or dispose of it, nor any containers associated with shipping, storing, handling, and disposing a treatment chemical, as is the situation with most chemicals utilized in water treatment.

The system 100 may be configured to provide indications pertaining to the operation status of the system 100, such as to ensure proper operation, or to provide an indication regarding a need for adjustment, servicing, or maintenance. For example, the flow switch 322 may be configured to send the signal to at least one indicator 222 that provides a visual, tactile, or audible indication that the fluid (e.g., water) is flowing through the fluid paths in the pipe assembly 300. In some embodiments, the indicator 222 is a light source (e.g., an LED) configured to illuminate upon receiving a signal from the flow switch 322. The indicator 222 may also be coupled to a sensor/relay (e.g., relay 210) configured to measure or detect whether a voltage is applied to the ozone generator 206. When a proper voltage is applied to the ozone generator 206, the sensor/relay can send a signal to the indicator 222. In some embodiments, the indicator 222 will provide a visual, tactile, or audible indication when each sensor and the flow switch 322 provide their respective signals to the indicator 222. For example, the system 100 can include a relay 210 coupled to the power supply unit 212 and the flow switch 322. The relay 210 may be configured to send an activation signal to the indicator 222 when the power supply unit 212 is providing power to the ozone generator 206 and when the flow switch 322 provides one or more signals regarding fluid flow through the system 100. In such a configuration, the indicator 222 can verify that the system 100 is operating under design conditions (e.g., having an active flow of water, and having a sufficient power supply to the ozone generator 206).

In some embodiments, the system 100 may include an in-line ORP sensor 128 positioned to measure the ORP of the aqueous ozone solution, such as adjacent a water output port, coupled within a distribution line, or the like. The in-line ORP sensor 128 can be coupled with the relay 210, such that the in-line ORP sensor 128 provides a signal to the relay 210 upon detection of a desired ORP or range of ORPs (e.g., in the range of 600 to 1000 mV, or other predetermined range). The relay 210 can then provide an activation signal to an indicator 222 upon proper functioning of the system 100 (e.g., when the power supply unit 212 is providing power to the ozone generator 206, when the flow switch 322 provide signals regarding fluid flow through the system 100, and when the in-line ORP sensor 128 detects a desired ORP of the aqueous ozone solution generated by the system 100). When the indicator 222 is not activated, this can provide an indication that a component or components of the system 100 may need adjustment, servicing, or maintenance. Alternatively, the system 100 can be configured to activate an indicator 222 upon failure of one or more of the components of the system 100 (e.g., no power supplied to the ozone generator 206, no flow of water detected by the flow switch 322, or an out-of-range ORP detected by the in-line ORP sensor 128).

By providing an ORP of between 600 mV and 1000 mV with the system, the output aqueous ozone solution can be utilized to destroy various pathogens, including, but not limited to, algae (e.g., blue-green), bacteria (e.g., *Aeromonas* & Actinomycetes, *Bacillus*, Campylobacters, *Clostridium botulinum, Escherichia coli* (*E. coli*), *Flavobacterium, Helicobacter* (*pylori*), Heterotrophic Bacteria, *Legionella pneumophila, Micrococcus, Mycobacterium tuberculosis, Pseudomonas aeruginosa, Salmonella, Shigella* shigellosis (dysentery), *Staphylococcus* sp, *albus, aureus, Streptococcus, Vibrio: alginolyticus, anguillarium, parahemolyticus, Yersinia enterocolitica*), fungi, molds, yeasts, mold spores, nematodes, protozoa (e.g., *Acanthamoeba* & *Naegleria,* Amoeboe Trophozoites, *Cryptosporidium, Cyclospora,* Entamobea (*histolytica*), *Giardia* lamblia, *Giardia muris, Microsporidium, N. gruberi*), trematodes, viruses (e.g., Adenovirus, Astrovirus, Cailcivirus, Echovirus, Encephalomyocarditis, Enterovirus, coxsachie, poliovirus, Hepatitis A, B and C, Myxovirus influenza, Norwalk, Picobirnavirus, Reovirus, Rotavirus).

The water in the aqueous ozone solution may have a surface tension of about 72 Millinewtons per meter at 20° C. as it enters the system. The system 100 may be configured to reduce the surface tension of the water in the aqueous ozone solution to about 48-58 Millinewtons per meter at 20° C. The reduced surface tension of the water enables the aqueous ozone solution being sprayed onto the hard surfaces and equipment to remove grease more effectively from hard surfaces and equipment since ozonated fluid is more capable of loosening and disintegrating any biofilm on the hard surfaces or equipment. The reduced surface tension of the water in the aqueous ozone solution better enables the cleansing of the hard surfaces and equipment since it more easily penetrates foreign material on the hard surfaces and equipment.

In some implementations, the system 100 may be used for water treatment or decontamination as described below.

Microbiological organisms/species can reside in water sources, including water intended for drinking recreation. Among the microbiological threats is the protozoan parasite—*cryptosporidium* (crypto). Crypto can be a particular challenge for the water treatment industry, however, ozone can eliminate it. Ozone, molecularly known as $O_3$, is a sanitizer and is relentless in its attack of organic microbes (bacteria, viruses, cysts, etc.). Through a process known as lysing, ozone breaks down cell walls or membranes, where it can then destroy the nucleus of the microbe. In addition to sanitation, ozone can provide for the oxidization of inorganic material that could be present in water, such as metals (e.g., iron and manganese). Although there are a few stronger oxidizers, ozone is the strongest that is readily available for commercial or residential use. For example, ozone is about 1.5 times stronger than chlorine, and can provide a faster oxidizing action. Furthermore, because of this higher oxidation strength, ozone does not build up a tolerance to microbes unlike other sanitizers, such as chlorine. Within the microbial world protozoa, such as crypto, are some of the most resistant to all types of disinfectants. One reason for this resistance is due to its hard outer protective shell, which must be broken through prior to the microbe being inactivated. Crypto can cause a variety of ailments, including abdominal cramping, diarrhea, fever, and nausea that can last as long as a month, according to the Centers for Disease Control and Prevention (CDC). Disinfectants used to ward off *cryptosporidium* for water treatment applications can include chlorine (liquid state), chloramines, chlorine-dioxide (gaseous state), and ozone. However, their ability to perform this inactivation duty should not be regarded equal, as each sanitizer requires a specific level of concentration and contact time to take effect, as described by the following.

To better determine the specific amount of the disinfectant required to inactivate or destroy a microbe, the Environmental Protection Agency (EPA) has determined Ct Values. These Ct Values are the product of the disinfectant's concentration (C, expressed in mg/L) and the contact time (t, expressed in minutes). These Ct Values are calculated specifically to the percentage of microbial kill or better known as the log reduction, e.g., 1-Log=90.0 percent, 2-Log=99.0 percent or 3-Log=99.9 percent inactivation of the particular microbe. According to the EPA, chlorine dioxide would require a Ct of 226, which would correlate to 226 mg/L, at one minute of contact time, at 25° C. to achieve a 3-Log reduction or 99.9 percent inactivation. Although, ozone would only require a Ct of 7.4, correlating to 7.4 mg/L, to achieve the same 99.9 percent inactivation with the same parameters as chlorine dioxide. Ct is a product of concentration and time, and as such, both can be manipulated, as long as the given Ct Value is obtained for the desired log reduction (e.g., Ozone Ct of 7.4 can be achieved with a concentration 3.7 mg/L for two minutes of time).

*Cryptosporidium* outbreaks in public drinking waters and recreational swimming pools are becoming an increasingly evident issue. Unfortunately, forms of chlorine sanitation are not often the best solution, especially for high organic and inorganic contaminant levels, as they will create chlorine oxidation by-products, such as trihalomethanes (THM) and chloramine derivatives. These by-products are the typical cause of (what most associate as being overchlorinated) the chlorine smell in drinking or pool waters, and are the cause of itchy, smelly skin and burning eyes in pool water. Although with a properly sized system, ozone can be used as the primary sanitizing and oxidizing agent, oxidizing the contaminants completely. Using ozone in this manner would then allow chlorine to be used as the secondary residual sanitizer to satisfy regulatory requirements, without the production of chloramines and chlorine's side effects.

Further, ozone can be used to remove iron and manganese from water, forming a precipitate that can be filtered:

$$2Fe^{2+}+O_3+5H_2O \rightarrow 2Fe(OH)_3(s)+O_2+4H^+$$

$$2Mn^{2+}+2O_3+4H_2O \rightarrow 2MN(OH)_2(s)+2O_2+4H^+$$

Ozone will also reduce dissolved hydrogen sulfide in water to sulfurous acid:

$3O_3 + H_2S \rightarrow 3H_2SO_3 + 3O_2$

The reactions involved iron, manganese, and hydrogen sulfide can be especially important in the use of ozone-based well water treatment. Further, ozone will also detoxify cyanides by converting the cyanides to cyanates (on the order of 1,000 times less toxic):

$CN^- + O_3 \rightarrow CNO^- + O_2$

Ozone will also completely decompose urea, where recent outbreaks of *E-coli* in lettuce have been impacted by urea:

$(NH_2)_2CO + O_3 \rightarrow N_2 + CO_2 + 2H_2O$

Ozonated fluids produced by the ozonated fluid dispensing system 100 were analyzed. During the production of the ozonated fluid, oxygen is drawn in through an ambient air dryer with the drying capacity to supply sufficient oxygen at a minus dew point to the generating system, the generating system accumulates excess volume of high-quality gas, which is stalled or held in the chambers, thereby supplying a consistent maximum volume of gas resulting in an ample supply of gas to the injecting system, thereby assuring zero cavitation at the point of gas-liquid interface. The pressure differential created by the fluid mixing paths reduces the size of the bubbles to a uniformed size bubbles with a spherical geometry that are entrained in the water, thereby lowering the surface tension of the processed fluid. This process makes the fluid act like a surfactant and reduces the surface tension from 72 Millinewtons per meter at 20° C. to a tested surface tension of 48-58 Millinewtons equal to 140° F. or 60° C. hot water. At liquid-gas interfaces, surface tension results from the greater attraction of liquid molecules to each other due to cohesion than to the molecules in the gas due to adhesion. The net effect is an inward force at its surface that causes the liquid to behave as if its surface were covered with a stretched elastic membrane. Thus, the surface becomes under tension from the imbalanced forces, which is probably where the term "surface tension" came from. Because of the relatively high attraction of water molecules for each other through a web of hydrogen bonds, water has a higher surface tension (72.8 Millinewtons per meter at 20° C.) compared to that of most other liquids. Surface tension is an important factor in the phenomenon of capillary action.

In embodiments, the ozonated fluid dispensing system 100 can be employed within any residential or commercial structure to supply aqueous ozone solution for cleansing, disinfecting, degreasing, and/or water treatment (e.g., water filtering, disinfecting, and/or softening). For example, the system 100 may be configured to receive water from a water source (e.g., a conventional water main/supply line, or the like) through inlet 116, mix the water with ozone, and dispense aqueous ozone solution through outlet 130. The system 100 may be used for a single application or a plurality of different applications. In residential or commercial applications, the system 100 may be configured to supply ozonated water to one or more taps that receive water from a main water source (e.g., the main water line). In this regard, the system 100 can be employed as a whole home or building water cleansing, disinfecting, degreasing, and/or water treatment solution. Alternatively, the system 100 may be used for a particular zone of a residential or commercial building. In some cases, a plurality of systems 100 can be used to ozonate water in a plurality of zones within a residential or commercial building.

The system 100 can also be used for a variety of applications including, but not limited to: cleansing and/or degreasing hard surfaces such as plastic, glass, ceramic, porcelain, stainless steel, or the like; cleansing and/or degreasing equipment such as food service equipment such as ovens, ranges, fryers, grills, steam cookers, oven stacks, refrigerators, coolers, holding cabinets, cold food tables, worktables, ice machines, faucets, beverage dispensing equipment, beer dispensers, shelving food displays, dish washing equipment, grease traps, or the like; and/or cleansing and/or degreasing HVAC or plumbing systems such as roof top units, air scrubbers, humidifiers, water heaters, water softeners, pumps, or the like. Other examples of equipment that can be coupled to the system 100 may include, but are not limited to, washdown stations (e.g., as described in U.S. Pat. No. 10,232,070), wall washing systems (e.g., as described in U.S. Pat. No. 10,232,071), vegetable and fruit washers (e.g., as described in U.S. Pat. No. 10,238,125), potato washers (e.g., as described in U.S. Pat. No. 10,231,466), carcass/subprimal cleaning systems (e.g., as described in U.S. Pat. Nos. 10,834,929 and 11,591,216), wastewater treatment systems, laundry washing machines (e.g., as described in U.S. Pat. Nos. 10,233,583 and 10,233,584), air scrubbers (e.g., as described in U.S. Pat. No. 11,352,256), pumps for pools, fountains, and other recreational/decorative water features (e.g., as described in U.S. Pat. No. 11,383,979). Furthermore, the system 100 can be used to supply aqueous ozone solution to a selected piece of equipment or to a combination of equipment (e.g., via multiple taps).

Although the invention has been described with reference to embodiments illustrated in the attached drawings, equivalents or substitutions may be employed without departing from the scope of the invention as recited in the claims. Components illustrated and described herein are examples of devices and components that may be used to implement embodiments of the present invention and may be replaced with other devices and components without departing from the scope of the invention. Furthermore, any dimensions, degrees, and/or numerical ranges provided herein are to be understood as non-limiting examples unless otherwise specified in the claims.

What is claimed is:

1. A system for generating aqueous ozone solution, comprising:
   an ozone generator;
   a relay configured to selectively activate the ozone generator by supplying an electrical current to the ozone generator;
   a variable resistor for controlling the rate of ozone output from the ozone generator by adjusting the electrical current supplied to the ozone generator from the relay; and
   a pipe assembly comprising:
      a first flow path for water to flow through, the first flow path including one or more ozone intake ports, the one or more ozone intake ports being fluidically coupled to the ozone generator, wherein the first flow path is defined by a first set of pipe segments and fittings between a water input port and a water output port of the pipe assembly;
      a second flow path fluidically coupled in parallel with the first flow path, the second flow path including a control valve that selectively permits a portion of the water to flow through the second flow path to produce a negative pressure in the first flow path so that ozone is drawn into the first flow path through the one or more ozone intake ports and mixed into the water flowing through the first flow path to produce an aqueous ozone solution, wherein the second flow path is defined by a second set of pipe segments and fittings that form a D shaped branch out of the first flow path; and
- a third flow path fluidically coupled in parallel with the first and second flow paths, wherein the third flow path includes a flow switch configured to transmit one or more control signals to the relay in response to sensing a flow of water, the relay being configured to supply the electrical current to the ozone generator in response to the one or more control signals.

2. The system of claim 1, wherein the variable resistor is a rheostat or a potentiometer.

3. The system of claim 1, further comprising:
- an oxygen concentrator configured to supply oxygen-enriched air to the ozone generator; and
- an air dryer configured to remove moisture from the oxygen-enriched air before the oxygen-enriched air is supplied to the ozone generator.

4. The system of claim 1, further comprising:
- one or more tubes for transferring ozone from the ozone generator to the pipe assembly; and
- a solenoid valve configured to purge residual ozone from the one or more tubes.

5. The system of claim 1, wherein the first flow path includes a fluid mixer removably coupled between two pipe fittings, wherein the fluid mixer comprises a multi-port coupler including a water inlet, a water outlet, and an ozone input port.

6. The system of claim 5, wherein the multi-port coupler includes a venturi.

7. The system of claim 1, further comprising:
- one or more oxidation reduction potential (ORP) monitors configured to detect an ORP of the aqueous ozone solution output by the pipe assembly.

8. The system of claim 1, wherein the control valve is adjustable to vary the negative pressure produced in the first flow path in order to control an ozone concentration of the aqueous ozone solution.

9. The system of claim 1, further comprising a transportable support frame for the system.

10. A system for generating aqueous ozone solution, comprising:
- an ozone generator;
- a relay configured to selectively activate the ozone generator by supplying an electrical current to the ozone generator;
- a variable resistor for controlling the rate of ozone output from the ozone generator by adjusting the electrical current supplied to the ozone generator from the relay; and
- a plurality of pipe assemblies, each of the pipe assemblies comprising:
  - a first flow path for water to flow through, the first flow path including one or more ozone intake ports, the one or more ozone intake ports being fluidically coupled to the ozone generator, wherein the first flow path is defined by a first set of pipe segments and fittings between a water input port and a water output port;
  - a second flow path fluidically coupled in parallel with the first flow path, the second flow path including a control valve that selectively permits a portion of the water to flow through the second flow path to produce a negative pressure in the first flow path so that ozone is drawn into the first flow path through the one or more ozone intake ports and mixed into the water flowing through the first flow path to produce an aqueous ozone solution, wherein the second flow path is defined by a second set of pipe segments and fittings that form a D shaped branch out of the first flow path; and
  - a third flow path fluidically coupled in parallel with the first and second flow paths, wherein the third flow path includes a flow switch configured to transmit one or more control signals to the relay in response to sensing a flow of water, the relay being configured to supply the electrical current to the ozone generator in response to the one or more control signals.

11. The system of claim 10, wherein the variable resistor is a rheostat or a potentiometer.

12. The system of claim 10, further comprising:
- an oxygen concentrator configured to supply oxygen-enriched air to the ozone generator; and
- an air dryer configured to remove moisture from the oxygen-enriched air before the oxygen-enriched air is supplied to the ozone generator.

13. The system of claim 10, further comprising:
- one or more tubes for transferring ozone from the ozone generator to the pipe assembly; and
- a solenoid valve configured to purge residual ozone from the one or more tubes.

14. The system of claim 10, wherein the first flow path includes a fluid mixer removably coupled between two pipe fittings, wherein the fluid mixer comprises a multi-port coupler including a water inlet, a water outlet, and an ozone input port.

15. The system of claim 14, wherein the multi-port coupler includes a venturi.

16. The system of claim 10, further comprising:
- one or more oxidation reduction potential (ORP) monitors configured to detect an ORP of the aqueous ozone solution output by the pipe assembly.

17. The system of claim 10, wherein the control valve is adjustable to vary the negative pressure produced in the first flow path in order to control an ozone concentration of the aqueous ozone solution.

18. The system of claim 10, further comprising a transportable support frame for the system.

* * * * *